United States Patent [19]

Giovanniello et al.

[11] Patent Number: 5,463,098
[45] Date of Patent: Oct. 31, 1995

[54] CLEAR ANTIPERSPIRANT GEL STICK AND METHOD FOR MAKING SAME

[76] Inventors: Rocco Giovanniello, 8 Painted Apron Ter., Port Jervis, N.Y. 12771; Nelson P. Ayala, 33 Euclid Ave., Middletown, N.Y. 10940

[21] Appl. No.: 110,086

[22] Filed: Aug. 20, 1993

Related U.S. Application Data

[63] Continuation-in-part of Ser. No. 977,070, Nov. 16, 1992, abandoned.

[51] Int. Cl.⁶ .............................. A61K 7/32; A61K 7/36; A61K 7/38; C07F 9/00
[52] U.S. Cl. ................... 556/27; 424/66; 424/67; 424/68; 556/34; 556/134
[58] Field of Search ................. 424/66, 68, 67; 556/27, 134, 34

[56] References Cited

U.S. PATENT DOCUMENTS

| | | | |
|---|---|---|---|
| 2,236,387 | 3/1941 | Wallace, Jr. et al. | 556/134 |
| 3,555,146 | 1/1971 | Jones et al. | 424/66 |
| 3,947,557 | 3/1976 | Jones et akl | 424/66 |
| 3,998,788 | 12/1976 | Rubino | 424/47 |
| 4,017,599 | 4/1977 | Rubino | 424/47 |
| 4,137,306 | 1/1979 | Rubino et al. | 424/68 |
| 4,774,079 | 9/1988 | Shin et al. | 424/66 |
| 4,781,917 | 12/1988 | Luebbe et al. | 424/67 |

FOREIGN PATENT DOCUMENTS

| | | | |
|---|---|---|---|
| 0175074 | 3/1986 | European Pat. Off. | A61K 7/32 |
| 0295071 | 12/1988 | European Pat. Off. | A61K 7/32 |
| 0404533 | 12/1990 | European Pat. Off. | A61K 7/32 |
| 2109685 | 6/1983 | United Kingdom | A61K 87/32 |
| WO15191 | 10/1991 | WIPO | A61K 7/38 |

*Primary Examiner*—Dale R. Ore
*Attorney, Agent, or Firm*—Anthony Lagani, Jr.

[57] ABSTRACT

A residue free, antiperspirant gel stick composition is disclosed which comprises an antiperspirant compound which is soluble in a diol, a normally liquid, water soluble diol, a gelling agent and a zinc glycinate in amount sufficient to control the pH of the gel stick at about 4.1 to about 5.0, the glycine to zinc mole ratio of the zinc glycinate added being about 2.0/1 to about 3.0/1. The process for preparing a diol soluble antiperspirant active useful in preparing the residue free gel stick is also disclosed and comprises reacting an antiperspirant compound with a water soluble, normally liquid diol in a water solution by heating for about 1 to about 100 hours at a temperature of about 50° C. to about 110° C.; adding a zinc glycinate to the reaction mixture and removing the water to recover a powdered antiperspirant active.

32 Claims, No Drawings

CLEAR ANTIPERSPIRANT GEL STICK AND METHOD FOR MAKING SAME

CROSS-REFERENCE TO RELATED APPLICATIONS

This application is a continuation-in-part of U.S. patent application Ser. No. 07/977,070 filed Nov. 16, 1992, now abandoned.

This invention relates to stick antiperspirant in a gel stick form. In particular it relates to process for preparing an antiperspirant active composition useful in preparing residue free gel sticks. The preferred gel sticks are clear, residue free antiperspirant gel stick.

BACKGROUND OF THE INVENTION

Gel stick antiperspirant and deodorant compositions are well known in the art. U.S. Pat. No. 4,346,079, discloses a clear gel stick utilizing dibenzyl sorbitol as a gelling agent and up to 10% of a propylene-ethylene glycol polycondensate. The invention purports to be an improvement over that of Dutch Patent Application No. 75.12239 which discloses an antiperspirant composition comprising 10–80 wt. % of lower monohydric alcohols, 10–60 wt. % of dihydric and/or trihydric polyols or lower polyglycols and 5–30 wt. % of propylene-ethylene glycol polycondensates. It is alleged in the '079 patent that such compositions have a sticky feel when applied to the skin. The improvement disclosed comprises deleting the polycondensates from the formulation and including an oleaginous compound in its stead. Mono and dialkyloamides are utilized as stabilizing agents.

U.S. Pat. No. 4,518,582, discloses acid stable monosorbitol gels. The composition combine a reactive solvent, a non-reactive solvent, dibenzylidene monosorbitol acetal as a gelling agent, $C_{12}$–$C_{20}$ fatty acids and a gel stabilizer consisting of magnesium sulfate, zinc acetate and hexamethylenetetramine. The reactive solvents are low molecular weight mono and diols, while the non-reactive solvents are those which contain less reactive secondary alcohol groups. The preferred reactive solvent is ethanol, and the preferred non-reactive solvents are 1,3 butylene glycol and 2,4-hydroxy-2-methyl pentane.

U.S. Pat. No. 4,781,917, discloses a gel stick utilizing an antiperspirant active, an emollient, a coupling agent and dibenzylidene monosorbitol acetal. The active compound is prepared by dissolving the antiperspirant into water and a polyhydric alcohol. The solution is then heated and the water removed, preferably by vacuum drying. It is alleged that the resulting antiperspirant active/polyhydric alcohol solution is clear. A polar solvent and an emollient of intermediate polarity are utilized in preparing a clear stick from the antiperspirant active solution. A buffering agent selected from the group consisting of sodium aluminum chlorhydroxyacetate, coconut monoethylamide, stearamide monoethanolamide and mixtures thereof.

U.S. Pat. No. 4,743,444, discloses a deodorant cosmetic stick which utilizes a $C_{14}$–$C_{20}$ fatty alcohol, e.g. Cetyl alcohol in conjunction with a liquid base and a benzylidene sorbitol as the gelling agent. The liquid base can comprise water, monohydric alcohols, polyhydric alcohols or mixtures of such alcohols. European Patent Application 0 404 532 (A1) discloses antiperspirant compositions comprising an antiperspirant active, a solvent comprising water, ethanol, propylene glycol, glycerine and mixtures thereof in conjunction with a co-solvent which carl comprise, inter alia, butylene glycol or liquid polyethylene and polypropylene glycols.

European Patent No. 0 404 533 (A1) discloses a liquid antiperspirant active comprising at least one powdered antiperspirant active containing a substantial amount of water associated with it and about 30 to 80 wt. % of at least one polyhydric alcohol comprising polyhydric alcohols containing 2–12 carbon atoms and 2 or more hydroxyl groups.

European patent application 0 451 002 A2 discloses gel stick compositions which rely on weakly basic organic nitrogen compounds as stabilizers for the composition. Generally, these stabilizers are amino-alcohol compounds such as 2-amino-2-hydroxymethyl-1,3-propanediol, 2-amino-2-methyl-1-propanol and N,N-tetrakis-2-hydroxypropyl-ethylene diamine. Other useful compounds include urea and imidazole. It is alleged that water and primary alcohols are not necessary components of the gel stick of the invention.

U.S. Pat. No. 3,904,741, discloses a method for preparing an alcohol soluble aluminum chlorhydrate by refluxing a water solution of the chlorhydrate and drying to a water content within a predetermined range.

There has been an increased demand for residue free, antiperspirant gel sticks, in particular clear, residue free antiperspirant gel sticks. The prior art clear gel sticks generally are found to be tacky to the touch or lack sufficient temperature stability to survive extended periods at elevated temperatures as might be found in warehouses or storage areas.

SUMMARY OF THE INVENTION

It has surprisingly been found that stable, clear antiperspirant gel sticks can be prepared utilizing zinc glycinate as the stabilizer for the composition. An antiperspirant active is prepared by dissolving an antiperspirant composition in water and heating to a temperature of about 50° to 100° C. Propylene glycol is then added and heating is continued at about 90° to about 110° C. Subsequently, zinc glycinate is added. The solution is spray dried and then redissolved into propylene glycol. This antiperspirant active solution is used to make a residue free antiperspirant gel stick. The gel stick can be clear.

The gel stick is prepared by mixing the propylene glycol solution with 1,3-butanediol, dipropylene glycol and a gelling agent, e.g. dibenzylidene monosorbitol acetal.

While the preferred antiperspirant gel sticks of this invention are clear they need not be so. The addition of various excipients such as emollients at higher levels, e.g. greater than ten percent (10%), result in antiperspirant which are opaque. They are nonetheless stable as a result of the inclusion of the zinc glycinate stabilizer, and are residue free.

Zinc glycinate is preferably added in an amount sufficient to raise the pH of the gel stick composition to about 4.1 to about 5.0. For a particular antiperspirant compound the pH of the system will be a function of the ratio of total metal to zinc, e.g., Al/Zn or Al+Zr/Zn. This ratio can be about 5 to about 50; Furthermore, the mole ratio of glycine to zinc in the zinc glycinate composition is preferably about 2.0/1 to about 3.0/1. In order that the glycinate be soluble in the stick formulation or the antiperspirant active composition to give a clear stick the glycine/zinc ratio is more preferably about 2.4/1 to about 3.0/1; typically, 2.4/1 to about 2.8/1, e.g. 2.5/1 to about 2.7/1, more specifically, 2.53/1.

DETAILED DESCRIPTION OF THE INVENTION

It is generally known that aluminum chlorhydrate gel sticks are unstable at pH level below 4.0 because the chlorhydrates or chlorhydrate/zirconium complexes hydrolyze at low pH to unstable solutions. At high pH levels on the other hand, the gels are stable but ineffective as antiperspirants. Similarly, the preferred gelling agent of the art, dibenzylidene monosorbitol acetal (Dibenzylidine Sorbitol, CSA No. 32647-67-9)(DBMA), hydrolyzes at low pH. A critical aspect of this invention comprises stabilizing the composition while retaining the effectiveness of the antiperspirant active by controlling the pH of the system with zinc glycinate. The zinc glycinate is utilized in an amount effective to adjust the pH of the system, which comprises an antiperspirant composition, at a pH level of about 4.1 to 5.0 pH, typically about 4.3 to about 5.0, e.g., about 4.4 to about 4.7. The pH of the system will depend on the particular antiperspirant composition utilized, e.g., aluminum/zirconium pentachlorhydrex-gly or tetra-chlorhydrex-gly, and the molar ratio of total metal to zinc derived from zinc glycinate, e.g., Al/Zn or (Al+Zr)/Zn. This ratio can be about 5/1 to about 50/1; typically about 8/1 to about 40/1, more typically, about 10/1 to about 36/1, e.g., about 14/1 to about 25/1. Furthermore, the mole ratio of glycine to zinc in the zinc glycinate composition is preferably about 2.0/1 to about 3.0/1. In order that theglycinate be soluble in the stick formulation or the antiperspirant active composition to give a clear stick the glycine/zinc ratio is more preferably about 2.4/1 to about 3.0/1; typically, 2.4/1 to about 2.8/1, e.g. 2.5/1 to about 2.7/1, more specifically, 2.53/1.

The antiperspirant compositions which can be utilized in the practice of this invention include aluminum halohydrates, zirconyl hydroxychlorides and complexes of aluminum halohydrates and zirconyl hydroxychlorides which may or may not contain glycine. The preferred halohydrates are the chlorhydrates. The preferred antiperspirant compositions are complexes of aluminum chlorhydrates and zirconyl hydroxychloride.

The aluminum halohydrate antiperspirant compositions are available in the form of polymeric compositions having the empirical formula:

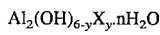

$$Al_2(OH)_{6-y}X_y \cdot nH_2O$$

wherein X is chlorine, bromine or iodine, y has a numerical value from about 0.7 to about 3 and n is a numeral having a value of about 0.8 to about 4.0. Preferably X is chlorine and y is 1. In another embodiment of the chlorhydrate, y is 2. Particularly preferred chlorhydrates are enhanced chlorhydrates having a high Band III component as measured by size exclusion chromatography. The preferred enhanced aluminum chlorhydrates have a Band III component of at least 25% component. See for example U.S. Pat. No. 4,359,456 to Gosling incorporated herein by reference. The most preferred enhanced aluminum chlorhydrates have no Band I component. See for example U.S. Pat. No. 4,871,525 to Giovanniello, incorporated herein by reference.

The zirconyl hydroxychlorides useful in the practice of this invention have the general formula $ZrO(OH)_{2-a}Cl_a \cdot nH_2O$ where "a" is about 1 to about 2, preferably about 1.5 to about 1.87 and "n" is about 1 to about 8. Both a and n can have non-integer values.

Other useful antiperspirants include aluminum chlorhydrate/zirconyl chloride/glycine complexes, generally known as "ZAG" complexes. See for example U.S. Pat. No. 4,871,525, referred to above, as well as U.S. Pat. Nos. 3,792,068, 4,120,948 and 4,775,528, all incorporated herein by reference, for methods of preparing the ZAG compounds.

The zirconyl hydroxychlorides are prepared by reacting $ZrCO_3$ with HCl in water. It will be appreciated by those skilled in the art that the empirical formula for a particular zirconyl hydroxychloride will depend upon the ratio of HCl to carbonate used in the reaction.

All of the antiperspirant compounds have varying amounts of water associated with them not withstanding the fact that they are "dry" powders. The water is present both as free water and as water of hydration.

A critical component in the preparation of the active antiperspirant compositions of this invention is zinc glycinate. Not wishing to be bound by theory, it is believed that the pH of the system having incorporated therein an antiperspirant composition is controlled at a pH of about 4.1 to about 5.0, typically 4.4 to about 5.0 by the zinc glycinate.

It is believed that at this pH level no destructive hydrolysis occurs; nor are the antiperspirant compounds deactivated. At high pH, antiperspirant compounds are less efficacious, while at low pH the antiperspirant compound as well as other components of the gel stick, e.g., dibenzylidine monosorbitol acetal, (DBMA) are hydrolyzed or react with other components of the stick composition. Surprisingly, the antiperspirant actives of this invention may be utilized with gel stick formulations wherein water and monohydric alcohols are utilized in the composition to form stable gel sticks. These agents ordinarily cause hydrolysis problems in prior art compositions.

The preferred gelling agent is dibenzylidene monosorbitol acetal (DBMA). This gelling agent as well as other gelling agents useful in the preparation of antiperspirant gel sticks are well known in the art for use in residue free, clear antiperspirant gel sticks.

In the practice of one embodiment of this invention a diol soluble antiperspirant active is prepared by dissolving an antiperspirant compound of the class described above into water to which propylene glycol and zinc glycinate are added. The solution is heated at about 50° to about 110° C. for about one to 100 hours and spray dried, typically about 5 to about 50 hours, e.g., about 15 to about 25 hours. At processing temperatures above 110° C. the product has an unacceptable "burned" odor. Not wishing to be bound by theory, it is believed that the odor is a result of decomposition of the glycine, though some odor may result from propylene glycol decomposition. The dried antiperspirant active powder can be redissolved into a diol, e.g., propylene glycol and utilized to prepare a clear antiperspirant gel stick. Concentrations of diol soluble antiperspirant active as high as 30–50 wt. % of the active in diol can be achieved. The concentration range of active in diol can vary from about 10 to about 50 wt. %, typically about 10 to about 40 wt. %, e.g. about 20–40 wt. %. The amount of material in the diol is a function of the diol. The preferred d/ol is propylene glycol (PG).

While the invention is described in terms of propylene glycol, other suitable dios can be utilized in the practice of this invention to prepare the antiperspirant active powder, and into which the powder can be redissolved. Illustrative, non-limiting examples of such diols are 1,3-butanediol, dipropylene glycol and PEG-4, a polyethylene glycol having a molecular weight of about 200. Generally, any water soluble, normally liquid diol can be used in the practice of this invention. The preferred diols are those normally liquid diols having at least one secondary alcohol in their structure, e.g., glycols such as propylene glycol. It is within the scope of this invention to utilize water soluble diols which are normally solid at room temperature, e.g., 1,6-hexanediol, 1,4-cyclohexanediol. In that event the solid diol will generally comprise a minor amount of the total diol utilized.

In the practice of this invention the atomic ratio of total metal to chloride of the antiperspirant compound in solution can be about 1.2/1 to about 2.0/1, e.g., 1.7/1–1.8/1. In the preparation of the zinc glycinate, the mole ratio of glycine to zinc can be about 2.0 to about 3.0, typically, 2.4/1 to about 2.8/1, e.g. 2.5/1 to about 2.7/1, more specifically, 2.53/1. It will be appreciated by those skilled in the art that, stoichiometrically, zinc can be associated with only two glycine moieties. However, zinc glycinate which has a gly/Zn ratio of 2.0, though available, is comparatively expensive. The excess glycine in the zinc glycinate forming reaction mixture drives the reaction toward a complete utilization of the ZnO reactant utilized in preparing the zinc glycinate. Not wishing to be bound by theory, it is believed that the excess glycine acts in part to lower the pH below that achieved by a specific amount of zinc glycinate having a gly/Zn ratio of 2.0. For example, a 5 wt. % zinc glycinate solution (gly/Zn =2.0) exhibits a pH of about 7.3. Where the gly/Zn ratio is 2.7 the pH is about 7.24. At a gly/Zn ratio of 3.0 the pH of the 5% solution is 7.11. Therefore, in adjusting the pH to the desired 4.1 to 5.0 range, it is necessary to take into account the gly/Zn ratio. Higher ratios may require greater amounts of the zinc glycinate solution in order to adjust the pH. Again, not wishing to be bound by theory it is believed that the glycine may advantageously act as a coupling agent to solublize the zinc glycinate to form clear gel sticks.

Where a zirconium/aluminum complex is utilized as the antiperspirant compound, the atomic ratio of aluminum to zirconium should be about 3.0 to about 10; preferably about 6/1 to about 9/1, e.g., 8.0/1.

In preparing the antiperspirant active composition the concentration of propylene glycol should be about 0.5 to about 3.75 times by weight that of the total metal found in the composition, typically about 1.0 to about 2.0, e.g. 1.24 times. The mole ratio of total metal of the antiperspirant active to zinc, i.e., aluminum or aluminum plus zirconium to zinc can be about 5/1 to about 50/1, typically about 8/1 to about 40/1, more typically, about 10/1 to about 36/1, e.g. about 15 to about 25/1. Where the antiperspirant compound is a pentachlorhydrex-gly the total metal to zinc ratio will typically be about 5/1 to about 25/1, e.g., about 10/1 to about 17/1, more specifically, about 12/1 to about 15/1. However, the foregoing ratios can be utilized for any antiperspirant compound, and the broader ranges are equally applicable to the pentachlorhydrex-gly. The solids content of the solution from which the antiperspirant active is prepared can be about 10 to about 55 wt. % solids, typically about 20 to about 40 wt. %, preferably about 25 to about 35 wt. %.

In preparing the zinc glycinate a preferred method comprises dissolving glycine in water at about 50° C. with stirring. The solution is then heated to about 70° C. and ZnO is added. The solution is further heated to about 95° C., and propylene glycol is added. Heating is continued at about 95° to 105° C. for about one hour, though heating may be continued until the solution is clear, e.g., about 6 hours. The zinc glycinate solution can comprise about 10 to about 20 wt. % of the zinc salt, typically about 10 to about 17 wt. %, e.g. 14 wt. %.

In carrying out the reaction for preparing the antiperspirant active of this invention utilizing an Al/Zr/gly complex it has been found that the temperature of the reaction can affect the viscosity of a propylene glycol solution prepared from the dried antiperspirant active powder of this invention redissolved in propylene glycol. At about a 40% solids content (including the propylene glycol associated with the dry powder) the solution will have a viscosity of about 700 to about 2,100 cps., where the reaction temperature is about 85°–95° C. On the other hand if the reaction temperature is about 101°–104° C., the viscosity of a similar solution prepared from the dried powder will have a viscosity of greater than about 5,000 cps. Where such higher viscosity solutions are the preferred product, the reaction temperature should be about 100° to about 110° C., e.g., 102°–106° C. Where the antiperspirant active is prepared by heating only an aluminum compound in the presence of glycol, without a zirconium compound present in the solution the same degree of viscosity increase is not observed.

As used in the specification and claims the term "antiperspirant active" means the dry powder reaction product of the process of this invention. The term "antiperspirant compound" means aluminum halohydrates, e.g., aluminum chlorhydrates; zirconyl hydroxychlorides and complexes thereof with glycine, complexes of aluminum chlorhydrates and zirconyl hydroxychlorides with or without glycine complexed therein and mixtures of the aforesaid compounds. It is within the scope of this invention to adjust the Al/Cl ratio by the addition of HCl or aluminum chloride hexahydrate ($AlCl_3$).

Throughout these examples the ratio of glycine to zinc (gly/Zn) is expressed as mole ratio, while the glycine to zirconium (gly/Zr) ratio is expressed as a weight ratio. The ratio of glycol to zinc, e.g., glycol/Zn is expressed as a mole ratio. Similarly, the ratio of metal to chloride is expressed in atomic or mole ratio, as is the ratio of metal in the antiperspirant active to zinc. Unless otherwise specified, percents are expressed in weight percent.

While the preparation of zinc glycinate is described in terms of the reaction of zinc oxide with glycine, those skilled in the art having access to this disclosure will appreciate that the analogous reactions of zinc chloride or zinc carbonate with glycine may be used to prepare the zinc glycinate. The carbonate reaction is somewhat slower than the oxide reaction and the chloride reaction has the disadvantage that HCl is produced as a byproduct.

EXAMPLE 1

Preparation of Antiperspirant Active

In a large round bottom flask 170 pounds of enhanced aluminum chlorhydrate (ACH) solution, 20.28 pounds of zirconyl hydroxychloride solution and 11 pounds of propylene glycol were mixed together and heated to about 85°–95° C. The ACH comprised a twenty percent solution of enhanced aluminum chlorhydrate sold by Westwood Chemical Corporation under its trademark Westchlor® DM 200 (WDM200). The zirconyl hydroxychloride solution comprised a 50 wt. % solution of a 1:1 weight ratio zirconyl hydroxychlorideglycine complex.

In a separate container, two pounds of zinc oxide, 4.5 pounds of glycine and 5.5 pounds of propylene glycol were blended together in 45.7 pounds of water which had been heated to 95° C. The mixture was held at 95° C. for about one hour, and then mixed with the solution of antiperspirant compositions described above. Heating was continued at about 96° C. for about two hours.

The hot solution which comprised about 30 wt. % solids was then spray dried in a conical bottom spray drier with an outlet temperature of about 212°–230° F. At temperatures below 212° F. the dried product contains sufficient moisture to cause it to stick to the walls of the drier and not flow freely. At drying temperatures above 230° F. the product has an undesirable odor and color. The operation of spray driers is well known to those skilled in the art and does not form a part of this invention.

The dried powder was taken up in propylene glycol to form a solution comprising 40 wt. % of the dried powder in propylene glycol. The dried powder contains the propylene glycol used in the reaction as well as the diol added to the solution from which the zinc glycinate was prepared. Not wishing to be bound by theory, it is believed that in the dried powder containing propylene glycol, at least a part of the propylene glycol of the reaction mixture is complexed with the antiperspirant compounds, and is relatively inseparable therefrom. This complexing is believed to render the antiperspirant active of this invention formed the process soluble in diols.

The solution was maintained at about 105° C. for about 2 hours. The solution was water white with a slight haze. About 250 grams of hyflo supercel filter aid was added to the solution which was then filtered. The resulting solution was clear and stable, and had a viscosity of about 760 cps.

Gel Stick Preparation

A gel stick was prepared utilizing the formulation shown in Table I.

TABLE I

| Component | % by wt. |
| --- | --- |
| DBMA | 2.5 |
| Antiperspirant Active* | 50.0 |
| Propylene Carbonate | 5.0 |
| Dipropylene glycol | 8.0 |
| PPG-10-butanediol | 2.0 |
| 1,3-butanediol | 32.0 |
| perfume | 0.5 |
| FDC Blue dye #1 | 2.4 mg. |

*The 40% solution described above prepared from propylene glycol and the dried powder antiperspirant active. If the total propylene glycol associated with the dried powder is subtracted out, the solids content is about 30 wt. %. The pH of a ten percent solution of the propylene glycol/antiperspirant active solution in water has a pH of 4.72.

Methods of preparing the antiperspirant gel sticks are known in the art. The following mixing procedure is illustrative of the methods used. Antiperspirant active, PPG-10-butanediol and the dye are blended together at 80° C. A second solution comprising the 1,3-butanediol heated to 110° C. is prepared with the addition of propylene carbonate and DBMA. The solution is heated to about 125° C. until the solution is clear. The second solution is then cooled to 110° C. and the first solution added with mixing . The perfume is then added, and after about five minutes of mixing the entire mixture is cooled to 81° C. and poured into gel stick dispensers. After about 5 minutes a stable clear gel was formed. The product exhibited both antiperspirant and deodorant properties. The total metal to zinc ratio was about 14.4/1.

EXAMPLE 2

Thirty four kg. of a 20 wt. % solution of enhanced aluminum chlorhydrate was added to a fifty liter round bottom flask with heating. 1.75 kg. of water were added to provide a solution with a chloride content of 3.38% chloride. The antiperspirant compound chromatogram showed that the enhanced aluminum chloride had a Band III content of 42.67%. Subsequently, 3.990 kg. of zirconyl hydroxychloride-gly was added with constant stirring. Then 2.256 kg. of propylene glycol was added. Heating was continued for three hours, over which time the temperature increased to 95° C.

After four and one-half hours a solution containing 14% zinc glycinate prepared in the manner described in Example I was added to the flask. Heating was continued at a higher level to bring the mixture to reflux. Reflux temperature was 103° C., and refluxing was continued for 2½ hours. The solution was then spray dried to dry powder.

In a 22 liter three necked flask 12.0 kg. of propylene glycol was added and heated to 90° C. The heated propylene glycol was then transferred to a five gallon pail. 8.0 kg. of the dried powdered antiperspirant active was slowly added over a forty-five minute period to the propylene glycol with stirring. A hand held homogenizer was used to thoroughly mix the solution.

The solution was returned to the 22 liter flask with stirring. The temperature had fallen to 60° C., but was increased to 90° C. with additional heating over a six hour period. 250 grams of Hyflo Supercel™ filter aid was added and the solution filter using a DR Sperry 0.3 ft³ filter press. The resulting product comprised 40 wt. % of antiperspirant active powder. The pH of a solution diluted to ten percent in water was 4.7. The total metal to zinc mole ratio was about 14.0/1.

EXAMPLE 3

The experiment of Example 2 was repeated using 36.62 kg. of 20% aqueous solution of enhanced aluminum chlorhydrate (Westwood WDM 200), 4010 grams of zirconyl hydroxychloride, a 14% solution of zinc glycinate prepared in the manner of Example 1 and 2.57 kg. of propylene glycol. The zirconyl hydroxychloride gly comprised a 1:1 ratio of zirconium to glycine each at about 18.70 wt. %, and having a chloride content of about 7.20 wt. %.

The zinc glycinate was prepared by reacting 0.422 kg. of ZnO, 0.971 kg. of glycine in , 8.0 kg. of water with heating at 95° C. until the solution was clear (about 2 hrs.) 1.183 kg. of propylene glycol was then added with heating for about an additional one-half hour. The resulting product had a glycine/Zn mole ratio of about 2.53/1, and a glycol/Zn mole ratio of about 3.0/1.

The solution was heated to reflux and refluxed for 16 hours at 103.7° C. Subsequently the product was spray dried using an inlet temperature of 500° F., and outlet temperature of about 220° F. The total metal to zinc ratio was about 14.6/1.

EXAMPLE 4

In a 12 l round bottom flask, 5.58 kg water was heated to 50° C. 0.646 kg. Glycine was added with stirring. The solution was heated to 75° C. and 0.263 kg. ZnO (gly/Zn mole ratio =2.7) was added with stirring was continued for 2 hours until ZnO is fully reacted. To achieve aglycol/Zn mole ratio of 3:1, 0.737 kg. propylene glycol was added and the solution was kept hot at 98° C.

22.7 kg. of a 20 wt. % solution of enhanced aluminum chlorhydrate (5.0 wt. % Al, 3.44 wt. % Cl, Al/Cl mole ratio=1.91, specific gravity=1.1146) at 80° C. was added to a 50 l round bottom flask fitted with a reflux condenser, mechanical glass stirrer, and a heating mantle. To achieve Al/Zr mole ratio of 8.0/1, 2.66 kg. of zirconyl hydroxychloride glycine (18 wt. % Zr, 6.75 wt. % Cl, 14.4 wt. % gly, Zr/C$_1$ mole ratio=1.0365, %gly/%Zr=0.8) was added to the round bottom flask. 1.41 kg. of propylene glycol was added and the entire batch was heated for 2 hours to achieve a temperature of 98° C.

The clear hot solution of zinc glycinate was added to the above solution and the entire solution was heated at 98° C. for 10 hours. The solution was removed to a 10 gallon polyethylene lined vessel, and spray dried at 540° F. inlet temperature, 220° F. outlet temperature. The total metal to zinc mole ratio was about 4.6/1.

EXAMPLE 5

In a 12 l round bottom flask, 5.58 kg. water was heated to 50° C. 0.646 kg. Glycine was added with stirring. The solution was heated to 75° C. and 0.263 kg. ZnO (gly/Zn= 2.7) was added with stirring was continued for 2 hours until ZnO is fully reacted. To achieve a glycol/Zn mole ratio of 3:1, 0.737 kg. propylene glycol was added and the solution was kept hot at 98° C.

9.19 kg. of a 50 wt. % solution of conventional aluminum chlorhydrate (ACH) (12.35 wt. % Al, 8.27 wt. % Cl, Al/Cl mole ratio=1.96, specific gravity=1.3383) at room temperature was added to a 50 l round bottom flask with a reflux condenser, mechanical glass stirrer, and a heating mantle. To achieve Al/Zr mole ratio=8.0, 2.66 kg. of zirconyl hydroxychloride glycine (18% Zr, 6.75 wt. % Cl, 14.4% gly, Zr/Cl=1.0365, %gly/%Zr=0.8) was added to the round bottom flask. 1.41 kg. of propylene glycol was added and the entire batch was heated for 2 hours to achieve a temperature of 98° C.

The clear hot solution of zinc glycinate was added to the above solution and the entire solution was heated at 98° C. for 10 hours. The solution was removed to a 10 gallon nalgene vessel, and spray dried at 540° F. inlet temperature, 220° F. outlet temperature. The total metal to zinc ratio was about 14.6/1.

EXAMPLE 6

In a 12 l round bottom flask, 5.58 kg. water was heated to 50° C. 0.646 kg. Glycine was added with stirring. The solution was heated to 75° C. and 0.263 kg. ZnO (gly/Zn= 2.7) was added with stirring which was continued for 2 hours until the ZnO was fully reacted. To achieve a glycol/Zn ratio of 3:1, 0.737 kg. propylene glycol was added and the solution was kept hot at 98° C.

22.7 kg. of a 20 wt. % solution of enhanced aluminum chlorhydrate (5.0% Al, 3.44%, Al/Cl=1.91, specific gravity =1.1146) at room temperature was added to a 50 l round bottom flask with a reflux condenser, mechanical glass stirrer, and a heating mantle. 1.41 kg. of propylene glycol was added and the entire batch was heated for 2 hours to achieve a temperature of 98° C.

The clear hot solution of zinc glycinate was added to the above solution and the entire solution was heated at 98° C. for 10 hours. The solution was removed to a 10 gallon nalgene vessel, and spray dried at 540° F. inlet temperature, 220° F. outlet temperature. The total metal to zinc ratio was about 13.0/1.

EXAMPLE 7

In a 12 l round bottom flask, 5.58 kg. water was heated to 50° C. 0.646 kg. Glycine was added with stirring. The solution was heated to 75° C. and 0.263 kg. ZnO (gly/Zn= 2.7) was added with stirring was continued for 2 hours until ZnO is fully reacted. To achieve a glycol/Zn ratio of 3:1, 0.737 kg. propylene glycol was added and the solution was kept hot at 98° C.

9.19 kg. of a 50 wt. % solution of conventional aluminum chlorhydrate (12.35% Al, 8.27%, Al/Cl=1.96, specific gravity =3383) at room temperature was added to a 50 l round bottom flask with a reflux condenser, mechanical glass stirrer, and a heating mantle. 1.41 kg. of propylene glycol was added and the entire batch was heated for 2 hours to achieve a temperature of 98° C.

The clear hot solution of zinc glycinate was added to the above solution and the entire solution was heated at 98° C. for 10 hours. The solution was removed to a 10 gallon nalgene vessel, and spray dried at 540° F. inlet temperature, 220° F. outlet temperature. The total metal to zinc ratio was about 13.0/1.

EXAMPLE 8

In a 12 l round bottom flask, 5.58 kg. water was heated to 50° C. 0.646 kg. Glycine was added with stirring. The solution was heated to 75° C. and 0.263 kg. ZnO (gly/Zn= 2.7) was added with stirring was continued for 2 hours until ZnO is fully reacted. To achieve a glycol/Zn ratio of 3:1, 0.737 kg. propylene glycol was added and the solution was kept hot at 98° C.

22.7 kg. of a 20 wt. % solution of enhanced aluminum chlorhydrate (5.0% Al, 3.44% Cl, Al/Cl=1.91, specific gravity=1.1146) at 80° C. was added to a 50 l round bottom flask with a reflux condenser, mechanical glass stirrer, and a heating mantle. The solution was heated to 98° C. To achieve Al/Zr=8.0, 2.28 kg. of zirconyl hydroxychloride (21% Zr, 7.88% Cl, Zr/Cl=1.0365) was added slowly, drop by drop to the round bottom flask with vigorous stirring. After 2 hours, 1.41 kg. of propylene glycol was added and the entire batch was stirred.

The clear hot solution of zinc glycinate was added to the above solution and the entire solution was heated at 98° C. for 10 hours. The solution was removed to a 10 gallon nalgene vessel, and spray dried at 540° F. inlet temperature, 220° F. outlet temperature. The total metal to zinc ratio was about 14.6/1.

EXAMPLE 9

In a 12 l round bottom flask, 5.58 kg. water was heated to 50° C. 0.646 kg. Glycine was added with stirring. The solution was heated to 75° C. and 0.263 kg. ZnO (gly/Zn= 2.7) was added with stirring was continued for 2 hours until ZnO is fully reacted. To achieve a glycol/Zn mole ratio of 3:1, 0.737 kg. propylene glycol was added and the solution was kept hot at 98° C.

9.19 kg. of a 50 wt. % solution of conventional aluminum chlorhydrate (ACH) (12.35% Al, 8.27% C, Al/Cl=1.96, specific gravity=1.3383) at room temperature was added to a 50 l round bottom flask with a reflux condenser, mechanical glass stirrer, and a heating mantle. To achieve Al/Zr=8.0, 2.28 kg. of zirconyl hydroxychloride (21.0% Zr, 7.89% Cl, Zr/Cl=1.0365) was added to the round bottom flask. 1.41 kg. of propylene glycol was added and the entire batch was heated for 2 hours to achieve a temperature of 98° C.

The clear hot solution of zinc glycinate was added to the above solution and the entire solution was heated at 98° C. for 10 hours. The solution was removed to a 10 gallon nalgene vessel, and spray dried at 540° F. inlet temperature, 220° F. outlet temperature. The total metal to zinc ratio was about 4.5/1.

EXAMPLE 10

In a 4 l round bottom flask, 0.558 kg. water was heated to 0° C. 0.0646 kg. Glycine was added with stirring. The solution was heated to 75° C. and 0.0263 kg. ZnO (gly/Zn= 2.7) was added with stirring was continued for 2 hours until ZnO fully reacted. To ultimately achieve an Al/Zr=8.0, 0.266 kg. of zirconyl hydroxychloride glycine (18% Zr, 6.75% Cl, 14.4% gly, Zr/Cl=1.0365, %gly/%Zr=0.8) was added to the 4 l round bottom flask. To achieve a glycol/Zn ratio of 3:1, 0.074 kg. of propylene glycol was added and the solution was kept hot at 98° C. for 10 hours with a reflux condenser attached. At the same time an additional 0.147 kg. of propylene glycol was added so that the final product would have a glycol content of about 20 wt. %.

The clear hot solution of zinc glycinate, zirconyl hydroxychloride glycine, and propylene glycol was added to 2.27 kg. of a 20 wt. % solution of enhanced aluminum chlorhydrate (5.0% Al, 3.44% Cl, Al/Cl=1.91, specific gravity =1.1146) at 80° C. and the entire solution was stirred, and spray dried in less than 20 minutes at 540° F. inlet temperature, 220° F. outlet temperature. The total metal to zinc ratio was about 14.6/1.

EXAMPLE 11

In a 4 l round bottom flask, 0.558 kg. water was heated to 50° C. 0.0646 kg. Glycine was added with stirring. The solution was heated to 75° C. and 0.0263 kg. ZnO (gly/Zn= 2.7) was added with stirring was continued for 2 hours until ZnO fully reacted. To achieve Al/Zr=8.0, 0.266 kg. of zirconyl hydroxychloride glycine (18 wt. % Zr, 6.75 wt. % Cl, 14.4 wt. % gly, Zr/Cl mole ratio= 1.0365, %gly/%Zr =0.8) was added to the 4 l round bottom flask. To achieve a glycol/Zn ratio of 3:1 the 0.074 kg. of propylene glycol was added and the solution was kept hot at 98° C. for 10 hours with a reflux condenser attached.

To 2.27 kg. of a 20 wt. % solution of enhanced aluminum chlorhydrate (5.0 wt. % Al, 3.44 wt. % Cl, Al/Cl mole ratio=1.91, specific gravity=1.1146) at 80° C. is added 0.141 kg. propylene glycol and heated at 98° C. for 10 hours. The three solutions were combined with stirring, and spray dried in less than 20 minutes at 540° F. inlet temperature, 220° F. outlet temperature. The total metal to zinc ratio was about 14.6/1.

EXAMPLE 12

In a 12 l round bottom flask, 5.58 kg. water was heated to 50° C. 0.646 kg. Glycine was added with stirring. The solution was heated to 75° C. and 0.263 kg. ZnO (gly/Zn= 2.7) was added with stirring was continued for 2 hours until ZnO is fully reacted. To achieve a glycol/Zn ratio of 3:1, 0.737 kg. propylene glycol was added and the solution was heated to achieve a temperature of 95° C., and was spray dried at an inlet temperature of 540° F., and an inlet temperature of 220° F.

22.7 kg. of a 20 wt. % solution of enhanced aluminum chlorhydrate (5.0% Al, 3.44% Cl, Al/Cl=1.91, specific gravity=1.1146) at 80° C. was added to a 50 l round bottom flask with a reflux condenser, mechanical glass stirrer, and a heating mantle. To achieve Al/Zr=8.0, 2.66 kg. of zirconyl hydroxychloride glycine (18% Zr, 6.75% Cl, 14.4% gly, Zr/Cl=1.0365, %gly/%Zr =0.8) was added to the round bottom flask. 1.41 kg. of propylene glycol was added and the entire batch was heated for 12 hours at a temperature of 98° C., and spray dried at 540° F. inlet temperature, 220° F. outlet temperature. The total metal to zinc ratio was about 14.6/1.

EXAMPLE 13

An antiperspirant active was prepared using the procedure of Example 1 except that no zirconyl hydroxy chloride or zinc glycinate was added. The concentration of the solution was about 40% aluminum chlorhydrate. Additionally, a 14% solution of zinc glycinate was prepared using the procedure of Example 1. The glycine/zinc mole ratio was 2.7:1. The following formulations shown in Table 2, were prepared using this antiperspirant active:

TABLE 2

| Component | Formulation A | Formulation B |
|---|---|---|
| Antiperspirant Active | 40.0g. | 40.0 g |
| PPG-5-Ceteth 20 | 8.0 | 8.0 |
| Zinc Glycinate Solution | 8.0 | — |
| 1,3- butanediol | 100.4 | 100.4 |
| Propylene carbonate | 2.0 | 2.0 |
| DBMA | 4.0 | 4.0 |
| Water | — | 6.88* |

*Water was added to compensate for the water contributed by the zinc glycinate solution.

The antiperspirant active solution was charged to a beaker and heated to 50° C. with constant stirring. The PPG-5-Ceteth 20 and zinc glycinate solution was then added, and the components heated to 78° C. In the case of Formulation B no zinc glycinate was added.

In a separate beaker the 1,3-butanediol and propylene carbonate were blended together and heated to 95° C. The DBMA was slowly added with continuous stirring, and the beaker contents heated to 127° C., until all of the DBMA was dissolved. The solution was then allowed to cool to 114° C., and the aluminum chlorhydrate solution added with stirring. The combined solution was allowed to cool to 80° C., at which time the solution was poured into clear antiperspirant barrels. The contents solidified in 15 minutes.

The samples with and without the zinc glycinate were heat aged for one week at 50° C., and checked for benzaldehyde odor as an indication of decomposition of the DBMA. The sample without zinc glycinate developed a strong benzaldehyde odor, while the zinc glycinate containing sample was odor free. The total metal to zinc ratio was about 35.1/1.

EXAMPLE 14

Zinc glycinate crystals were prepared by drying the 14% zinc glycinate solution in an oven over night at 85° C.

Thirty grams of an enhanced aluminum chlorhydrate powder (Westchlor® DM 200) was dissolved into 70.0 g. of propylene glycol with stirring at 90° C. until the solution was practically clear. 8.0 g. of water and 7.8 grams of zinc glycinate crystals were added. After about 90% of the zinc glycinate had dissolved, the clear supernatant solution was transferred to a clean beaker by decanting while maintaining temperature at 90° C.

In a separate beaker 73.2 grams of polyethylene glycol (PEG 4 was charged together with 2 grams of propylene carbonate. The solution was heated to 95° C. and 4.0 grams of DBMA slowly added with continued heating to 126° C. until all of the gelling agent dissolved. The solution temperature was lowered to 112° C. and 3.0 grams of PPG-2-Isodeceth 12 were added.

The aluminum chlorhydrate/zinc glycinate solution was added to the DBMA solution with stirring, and the combined solution was allowed to cool to 80° C. The solution was then poured into molds, and a solid clear gel formed after one hour of standing. The total metal to zinc ratio was about 12.9/1.

EXAMPLE 15

In this illustration of the invention an Al/Zr/gly complex is formed wherein only the aluminum compound is reacted with the propylene glycol. Three separate experiments were run using the same quantity of reactants. Only the step in which the zirconyl hydroxychloride-glycinate (Zr(O)(OH)Cl-gly) is added is varied by changing the temperature at which the addition is made. The total metal to zinc ratio was about 14.8/1. The formulation is shown in Table 3.

TABLE 3

| Reactants | Pounds |
| --- | --- |
| Water | 93.0 Pounds |
| Propylene Glycol (PG) | 10.0 |
| 50% solution of ACH | 62.0 |
| Zr(O)(OH)Cl-gly | 17.43 |
| ZnO | 1.766 |
| Glycine | 4.337 |
| Water | 35.0 |
| Propylene Glycol | 4.95 |

A. Preparation of Zinc Glycinate

Thirty five (35.0) pounds of water were added to a 22 liter vessel and heated to 90° C. Glycine (4.337 lbs.) was then added with stirring, and the solution was heated to 95° C. Zinc oxide (1.766 lbs.) was then added with stirring and heating continued for two hours until the solution was clear (gly/Zn=2.7/1; PG/Zn=3.0/1). Propylene glycol (4.94 lbs.) was then added and heating continued for an additional one-half hour.

B. Reaction of Aluminum chlorhydrate (ACH) and Propylene Glycol

Ninety three (93.0) pounds of water and sixty two (62.0) pounds of 50 wt. % ACH solution were heated to 90° C. in a 30 gallon glass lined reactor for 19 hours. Ten (10.0) pounds of propylene glycol (PG) were added and the temperature increased to 101.3° C. Heating was continued for 46 hours. The steam heat source was then shut off and the ACH/PG solution was allowed to cool to below 60° C.

C. Combination of Reactants

After 10 hours of standing 17.43 pounds of zirconyl hydroxy chloride/gly was added to the ACH/PG solution over a period of 5 minutes with continuous stirring. After three hours with the solution at 45° C. the zinc glycinate solution at 95° C. was slowly added over a five minute period. The temperature of the entire mixture was maintained at 45° C. for about two hours. The solution was cooled to room temperature. The pH of the solution was 4.7. The product was dried using a high pressure single fluid nozzle with a drier inlet temperature of 560° F. and an outlet temperature of 220° F.

D. Twenty-nine pounds of the dried powder was dissolved into 35 pounds of propylene glycol at 60° C. The solution was then heated to 95° C. and maintained at that temperature for eight hours. After filtering the hot solution with plate and frame filter press the solution was cooled to room temperature.

EXAMPLE 16

Example 15 was repeated except that in step C the reaction mixture was maintained at 80° C. instead of 45° C.

EXAMPLE 17

Example 15 was repeated except that in Step C the reaction mixture was maintained at 60° C. instead of 45° C.

EXAMPLE 18

Example 15 is repeated except that in Step C the reaction mixture is maintained at 80° C. instead of 45° C., and the zinc glycinate is added before the zirconyl hydroxy chloride. Additionally, the zirconyl hydroxy chloride is added and the solution spray dried within about fifteen (15) minutes after addition of the zirconyl hydroxy chloride.

EXAMPLE 19

The antiperspirant active of this invention was prepared using the following materials:
80.7 lbs. of 50% aqueous aluminum chlorhydrate
(12.44% Al, 8.32% Cl, Al/Cl=1.96)
120 lbs. of water
12.0 lbs. propylene glycol
56.0 lbs. zirconyl hydroxychloride-gly
(17.3% Zr, 9.32% Cl, 12.1% glycine)

The aluminum chlorhydrate, water and propylene glycol were mixed together and heated to 101° C. for 24 hours, under moderate reflux with constant stirring, in a steam jacketed glass lined reactor. No water was lost during heating. The steam heat was then turned off and the solution was allowed to cool to 70° C. in about 5 hours. Cooling water was introduced into the reactor jacket, bringing the solution temperature down to about 40° C. 56 lbs. of zirconyl hydroxychloride was then added to the solution with constant stirring. The entire contents of the glass lined reactor was then transferred to a nalgene container, and hot zinc glycinate solution was siphoned into it with constant stirring.

The zinc glycinate was prepared as follows:

Sixty pounds of water was added to a 50 liter round bottom flask, and the temperature increased to 75, C using an electric heating mantle. Glycine (7.36 lbs.) was slowly added with continuous stirring until the solution was clear. Zinc oxide (3.0 lbs.) was then added with continuous stirring, and the temperature was increased to 95° C. stirring was continued until the solution was once again clear. Finally, 8.41 pounds of propylene glycol was added and the entire mixture stirred until the solution was clear. The clear zinc glycinate/propylene glycol/water solution was then siphoned into the nalgene container, and the solution was spray dried.

A 24 wt. % solution of antiperspirant active was prepared by dissolving 74 lbs. of the powder into 151 lbs. of propylene glycol at 75° C. The solution was heated with continuous stirring to 92° C., and maintained at that temperature for six hours with constant stirring to fully dissolve all of the powder. The solution was then filtered using a plate and frame press using Hyflo filter aid to obtain a clear 24 wt. % active. The product was a tetrachlorhy-drex-gly having the following analysis:
Al/Zr=3.56; (Al+Zr)/Cl=1.41; (Al+Zr)/Zn=13.88; pH=4.21 (10% w/w)

EXAMPLE 20

A modified product similar to that of Example 19 was prepared utilizing about one-half of the amount of zinc glycinate in the following manner using as raw materials:
4.0 Kg. of 50% aqueous aluminum chlorhydrate
(12.38% Al, 8.43% Cl, Al/Cl=1.93)
6.0 Kg. of water
0.5 Kg. propylene glycol
1.148 Kg. Zirconyl hydroxychloride-gly
18.4% Zr, 7.15% Cl, 16.6%glycine)

The aluminum chlorhydrate, water and propylene glycol were mixed together and heated to 101.7° C. in a 12 liter round bottom flask for 31 hours. Reflux condensers were used so that no water was lost during the heating cycle. Heating was then turned off and the solution was allowed to cool to 70° C. The zirconyl hydroxychloride was then added to the solution with constant stirring. Heating was continued to maintain the temperature at 70° C. for 16 hours. Hot zinc glycinate solution was slowly added with constant stirring.

The zinc glycinate was prepared as follows:

1.150 Kg. of water was added to a 4 liter round bottom flask, and the temperature increased to 75° C. using an electric heating mantle. Glycine (0.143 Kg.) was slowly added with continuous stirring until the solution was clear. Zinc oxide (0.058 Kg.) was then added with continuous stirring, and the temperature was increased to 95° C. stirring was continued until the solution was once again clear. Finally, 0.163 Kg. of propylene glycol was added and the entire mixture stirred until the solution was clear. The clear zinc glycinate/propylene glycol/water solution was then transferred to the twelve liter round bottom flask. After thorough mixing the solution was spray dried to recover the antiperspirant active powder.

A 34 wt. % solution of antiperspirant active was prepared by dissolving 2013 grams of the powder into 2545 grams of propylene glycol at 95° C. The solution was maintained at 95° C. with continuous stirring, and maintained at that temperature for three hours. The solution was then filtered through Whatman #4 filter paper pre-coated with Hyflo filter aid to obtain a clear 34 wt. % active. The product was a pentachlorhydrex-gly having the following analysis:

Al/Zr=7.7; (Al+Zr)/Cl=1.78; (Al+Zr)/Zn=34.8 pH=4.40 (10% w/w)

The invention has generally been described in terms of spray drying to recover an antiperspirant active powder with redissolving of the powder in a diol, preferably a glycol. It is within the scope of this invention, however, to remove water from the solution in which the antiperspirant active is prepared, by distillation of the water from the system. The result is that the antiperspirant active remains in solution in a water free system, ready for use in the preparation of antiperspirant gel sticks. The method used for removing the water from the active, e.g., spray drying or distillation, will depend on the facilities available for drying. Where spray drying equipment is already on site, the investment in vacuum distillation equipment may not be justified by the savings in avoiding the need for redissolving of the antiperspirant active. The preparation of antiperspirant active utilizing distillation to remove water is exemplified in Example 21.

EXAMPLE 21

Sixty (60) pounds of water, 5 lbs. of propylene glycol and 40 lbs. of 50% aluminum chlorhydrate solution were added to a glass lined reactor, and heated at 101° C. under reflux conditions for 24 hours. The solution was cooled down to 70.0° C. over a five hour period. 12.7 lbs. of zirconyl hydroxychloride-gly (Zr- 17.3 wt. %, Cl-6.72%, Gly-15.7%; %Gly/%Zr=0.91, Zr/Cl=1:1) were added slowly with stirring and the temperature maintained at 70.0° C. for twelve hours. The vessel was then cooled over a twelve hour period to below 40° C. 14 lbs. of a 14% w/w solution of zinc glycinate (23 lbs. $H_2O$, 2.85 lbs. glycine, 1.15 lbs. ZnO) were added slowly to the glycol/chlorhydrate solution with constant stirring. Sixty five pounds of propylene glycol were then added to the reaction vessel.

Water was removed by distillation. A vacuum of 481.33 mm Hg (19" Hg) was used at 70° C. Reflux and water removal began after the temperature was raised to 70.0° C. To continue the distillation it was necessary to slowly raise the temperature to 80° C. A vacuum of 608 mm Hg (24" Hg) at 70° C. was utilized to remove the last traces of water. 100 lbs. of 30% w/w antiperspirant active in propylene glycol was recovered as product. The progress of the distillation was monitored by measuring the refractive index of the distillate throughout the distillation process (RI $H_2O$=1.333 at 25° C., RI propyleneglycol=1.432 at 25° C.)

The product was useful in preparing clear antiperspirant gel sticks.

Effect of Reaction Time and Temperature

Where the antiperspirant composition is Al/Zr/gly, the viscosities of the propylene glycol solution containing about 30 wt. % of the dissolved antiperspirant active powder ranged between 600 cps and 15,000 cps, depending upon the time and temperature used for heating the feed solution prior to spray drying. The temperature used for heating the solutions varied between 95° C. and 104° C. The viscosity of the finished propylene glycol solution was increased in a very reproducible and consistent fashion by increasing the temperature of heating in the feed solution. The effect of increasing the time also was to increase the viscosity of the solution obtained by dissolving powder in propylene glycol, but after 48 hours the effects of prolonging the time are less pronounced.

Typical Procedure for Dissolving Powders

Propylene glycol is heated to at about 60° C. to about 90° C., e.g., 80°–85° C., in order to lower viscosity and speed the rate of dissolving the antiperspirant active powder. The temperature is kept less than 100° C. in order that the powder will not burn in the mixing vessel. Enough powder is dissolved to make a 40% w/w solution. Powder is added gradually with an Accu-feeder. Meanwhile the solution is stirred vigorously, preferably using a stirring motor which can provide at least 10 in-lb of torque.

When using mechanical stirring with teflon mixing blades, the rate of stirring is about 30 rpm, to about 180 rpm, e.g., 120 rpm. An Epenbach high shear mixer can also be used to obtain efficient mixing prior to filtration. Depending on the rate of stirring and the amount of shear, between 2–6 hours of mixing is required to dissolve substantially all of the powder in propylene glycol.

Typical Procedure for Filtration of Solutions

Prior to filtration the solution is adjusted with propylene glycol to achieve a final concentration of 30% w/w solids. Solutions are filtered hot to maintain lower viscosity. A D. R. Sperry 0.3 cu. ft. plate and frame filter press can be used with Hyflo Supercel® filter aid (diatomaceous earth). A compressed air drive reciprocal pump is used to pump the liquid through the press.

It will be appreciated by those skilled in the art that the use of zinc glycinate to control pH is essential, but the point of addition of the zinc glycinate is not. While the examples have generally illustrated the addition of zinc glycinate to the antiperspirant compound while heating in the presence of propylene glycol it is within the scope of this invention to add the zinc glycinate solution to the antiperspirant/propylene glycol solution immediately before spray drying. Additionally, the zinc glycinate may be spray dried separately, and blended with the other dried powder or added to the reconstituted powder in the propylene gly col. Furthermore, it is within the scope of the invention to add the zinc glycinate as a powder or solution directly to the gel stick formulation.

Similarly, the zirconyl hydroxychloride need not be heated in the presence of the halohydrate and propylene glycol. Instead it may be added to the halohydrate/propylene glycol solution before the spray drying step, e.g., immediately before spray drying.

While throughout the examples propylene glycol is used as the diol it will be appreciated by those skilled in the art that any of the class of diols, particularly glycols, can be utilized in the practice of this invention. The antiperspirant active powder of this invention may be stored in either the dried state or as the filtered, stable diol solution. Where the dried powder is dissolved into a diol prior to the formulation of a residue free gel stick it is preferably filtered. Filtration is essential if the solution is hazy to ensure that the product is a clear antiperspirant gel stick.

The aluminum/zirconium antiperspirant complexes can be trichlorhydrex-glys, tetrachlorhydrex-glys, pentachlorhydrex-glys or octachlorhydrex-glys.

While the invent/on has been described, generally, in terms of a clear gel stick, it will be appreciated by those skilled in the art having access to this disclosure that the antiperspirant active of this invention is useful in the preparation of any stable, residue free antiperspirant gel stick whether or not it is clear. For example, the addition of more than 10 wt. % emollient can result in a gel stick which is residue free, but not clear.

It will be further appreciated by those skilled in the art that the zinc glycinate of this invention can be utilized to stabilize any antiperspirant gel stick utilizing a diol soluble antiperspirant compound of the prior art by controlling the pH of the gel stick composition at about 4.4 to about 5.0, e.g., about 4.4 to about 5.0.

While any commercially available zinc glycinate (gly/Zn=2.0) can be used, it is preferred that additional glycine be added to increase the gly/Zn ratio to about 2.4 to about 3.0, e.g., 2.4 to about 2.8.

The zinc glycinate prepared in situ in the practice of this invention is generally described as being prepared utilizing propyleneglycol in the heating step. While it is not essential to add a diol to the zinc glycinate reaction mixture, doing so appears to improve compatibility with the diol containing gel stick formulation.

The amount of zinc glycinate required to raise the pH of the antiperspirant containing composition will depend on the type of antiperspirant utilized and its concentration in the solution or gel stick. Generally where the ratio of glycine to zinc is about 2.0/1 to about 3.0/1 about 12 wt. % to about 30 wt. % of zinc glycinate based on antiperspirant plus zinc glycinate is utilized. It is preferred that instead of relying on a calculated weight of glycinate to adjust pH, the weight addition is used as a first approximation, generally underdosing, followed by measurement of the pH and gradual addition of glycinate if necessary until the desired pH is achieved. Alternatively, the amount of zinc glycinate added is determined based on the total metal to zinc ratio desired, and pH measured as a check to ensure that the proper range is achieved. It will be appreciated by those skilled in the art having access to this disclosure that once a particular formulation is settled on for a particular batch of antiperspirant and zinc glycinate, weight measurements are sufficient to achieve the desired pH level. In order that pH values are consistent and reproducible the measurements are made by diluting the antiperspirant active/propylene glycol solution with water to a 10 wt. % solids concentration.

Formulations for antiperspirant gel sticks are well known in the art. These compositions include emollients, emulsifiers, carriers, coupling agents and gelling agents. While numerous compounds have been known as gelling agents, including soaps and waxes, the preferred gelling agent is dibenzylidene monosorbitol acetal (DBMA), otherwise known as dibenzaldehyde monosorbitol acetal. Depending on the gelling agent selected it can comprise about 1% to about 30% of the stick composition. The DBMA can comprise about 1% to about 15% of the stick composition; generally, about 1.5% to about 4.5%.

The carriers act as solvents for the antiperspirant stick compositions and can include polyhydric alcohols. These compounds include propylene glycol, butylene glycol, glycerine and dipropylene glycol. Minor amount of water can be included in the carrier. The carrier can comprise abut 5% to about 85% of the stick composition. The carrier acts as the solvent for the other components of the gel stick composition.

Emulsifiers, or coupling agents, are used to bring polar and non-polar components of the stick into a homogeneous mixture. Emulsifiers include polyethylene glycol, polypropylene glycol, ethers of $C_4$–$C_{22}$ fatty alcohols and $C_{12}$–$C_{15}$ alcohol lactate. The emulsifier can comprise 5% to 60% of the stick composition. It will be appreciated by those skilled in the art that when the polyalkylene glycols are used in large quantities they act as both emulsifiers and carriers.

Emollients are used to provide a dry feel and reduce tackiness. Suitable emollients include volatile and non-volatile silicones, fatty alcohols, and $C_{12}$–$C_{15}$ alcohol lactares. Emollients can be utilized at about 2% to 30%.

While these formulations for antiperspirant gel stick compositions are old in the art applicants use of zinc glycinate to control pH for the purpose of stabilizing the gel stick is novel.

What is claimed is:

1. A process for preparing a diol soluble antiperspirant active useful in the preparation of a stable, clear, antiperspirant gel stick which comprises reacting an antiperspirant compound with a water soluble, normally liquid diol in a water solution by heating for about 1 to about 100 hours at a temperature of about 50° C. to about 110° C.; adding a zinc glycinate to the reaction mixture in an amount such that the ratio of total metal to zinc is about 8/1 to about 40/1, the mole ratio of glycine to zinc being about 2.4/1 to about 3.0/1, and removing the water to recover a powdered antiperspirant active.

2. The process according to claim 1 wherein the water is removed by spray drying the solution to recover a powdered antiperspirant active.

3. The process according to claim 1 wherein the water is removed by distillation to recover a solution of antiperspirant active in the normally liquid diol.

4. The process according to claim 1 wherein the antiperspirant compound comprises an aluminum-zirconium pentachlorhydrexgly or tetrachlorhydrex-gly prepared in situ by reacting a zirconyl hydroxychloride with an aluminum containing chlorhydrate antiperspirant compound in the water solution of the normally liquid diol.

5. The process according to claim 1 wherein the diol contains at least one secondary hydroxyl group.

6. The process according to claim 1 wherein the diol is a glycol, a polyalkylene glycol or 1,3-butanediol.

7. The process according to claim 6 wherein the glycol is propylene glycol.

8. The process according to claim 6 wherein the polyalkylene glycol is polyethylene glycol or polypropylene glycol.

9. The process according to claim 1 wherein the process temperature is about 85°–95° C.

10. The process according to claim 1 wherein the process temperature is about 100°–110° C.

11. The process according to claim 1 wherein the process temperature is about 102°–106° C.

12. The process according to claim 1 wherein the heating is carried out over about 5 to 50 hours.

13. The process according to claim 1 wherein the heating is carried out over about 15 to 25 hours.

14. The process according to claim 1 wherein the antiperspirant compound is an aluminum/zirconium complex and the Al/Zr atomic ratio is about 3.0 to about 10.

15. The process according to claim 1 wherein the Al/Zr atomic ratio is about 6 to about 9.

16. The process according to claim 1 wherein the mole ratio of total metal of the antiperspirant compound to zinc is about 12/1 to about 15/1.

17. The process according to claim 1 wherein the total metal to chloride atomic ratio is about 1.2/1 to about 2.0/1.

18. The process according to claim 1 wherein the total metal to chloride atomic ratio is about 1.7/1 to about 1.8/1.

19. The process according to claim 1 wherein the antiperspirant compound is an aluminum chlorhydrate, a zirconyl hydroxychloride or an aluminum-zirconyl hydroxychloride complex.

20. The process according to claim 19 wherein the antiperspirant compound is an enhanced aluminum chlorhydrate.

21. The process according to claim 19 wherein the antiperspirant compound is an aluminum-zirconium tetrachlorhydrex-gly.

22. The process according to claim 19 wherein the antiperspirant compound is an aluminum-zirconium pentachlorhydrex-gly formed in situ from an aluminum chlorhydrate and a zirconyl hydroxychloride-gly.

23. The process according to claim 22 wherein the zirconyl hydroxychloride is a zirconyl hydroxychloride-gly.

24. The process according to claim 1 wherein the zinc glycinate is prepared in situ from a zinc oxide-glycine water solution containing a diol.

25. The process according to claim 24 wherein the solution is heated for about 1 to about 30 hours at a temperature of about 70° to about 110° C.

26. The process according to claim 24 wherein the diol contains at least one secondary hydroxyl group.

27. The process according to claim 24 wherein the diol is a glycol, a polyalkylene glycol or 1,3-butanediol.

28. The process according to claim 27 wherein the glycol is propylene glycol.

29. The process according to claim 27 wherein the polyalkylene glycol is polyethylene glycol or polypropylene glycol.

30. The process according to claim 24 wherein the glycine/zinc ratio is about 2.4/1 to about 2.8/1.

31. The process according to claim 1 wherein the moles of diol utilized is about 1 to about 3.75 times the weight of total metal in the antiperspirant compound utilized.

32. The product prepared according to the process of claim 1.

* * * * *